United States Patent
Piltch et al.

(10) Patent No.: US 6,469,794 B1
(45) Date of Patent: Oct. 22, 2002

(54) HIGH RESOLUTION NON-CONTACT INTERIOR PROFILOMETER

(76) Inventors: Martin S. Piltch, 2915 Arizona Ave., Los Alamos, NM (US) 87544; R. Alan Patterson, 416 Cheryl Ave., Los Alamos, NM (US) 87544; Gerald W. Leeches, 1918 Mendius Land, Los Alamos, NM (US) 87544; John Van Nierop, 13656 Kimerly Oaks Cir., Largo, FL (US) 33774; John J. Teti, Jr., 3315 W. Lawn Ave., Tampa, FL (US) 33611-1930

(*) Notice: Subject to any disclaimer, the term of this patent is extended or adjusted under 35 U.S.C. 154(b) by 0 days.

(21) Appl. No.: 09/895,617

(22) Filed: Jun. 28, 2001

(51) Int. Cl.$^7$ .............................................. G01B 11/24
(52) U.S. Cl. ..................................................... 356/601
(58) Field of Search ................................ 356/601, 626, 356/612

(56) References Cited

U.S. PATENT DOCUMENTS 6,229,617 B1 * 5/2001 Piltch et al. ................ 356/477

* cited by examiner

Primary Examiner—Scott J. Sugarman
(74) Attorney, Agent, or Firm—Milton D. Wyrick

(57) ABSTRACT

Apparatus and method for inspecting the interior surfaces of devices such as vessels having a single entry port. Laser energy is introduced into a device under test and to a time delay. Light reflected from the interior surfaces of the device under test is introduced into one end of a dye-cell and the time-delayed light is introduced into the other end. The amount of time delay is adjusted to produce two-photon fluorescence in the dye-cell so that the amount of time delay is representative of the interior surfaces of the device under test.

21 Claims, 5 Drawing Sheets

HIGH RESOLUTION NON-CONTACT INTERIOR PROFILOMETER

BACKGROUND OF THE INVENTION

The present invention generally relates to procedures for inspecting the condition of manufactured articles, and, more particularly to the inspection of the interiors of manufactured articles such as tanks, medical implants, turbines, and other closed applications in which only limited access is provided. This invention was made with Government support under Contract No. W-7405-ENG-36 awarded by the U.S. Department of Energy. The Government has certain rights in the invention.

Inspection of manufactured articles is of great importance, particularly to manufacturers of critical equipment whose failure can produce catastrophic results. However, some of the articles in this category defy close inspection because the geometry of the article makes inspection extremely difficult for conventional inspection techniques.

Fiber optical devices are used extensively to view objects that normally would be considered inaccessible. The optical fiber elements for this purpose are typically smaller than 50 $\mu$m in diameter, including protective layers. Optical fibers such as these can be bent into radii as short as 3 cm, allowing their infiltration into areas that normally preclude direct imaging techniques.

The medical community has made extensive us of such optical fibers for endoscopic applications, such as the real-time imaging of internal organs to provide guidance for microsurgical techniques. Fiber-optic technology also has been applied in many other areas, such as opto-mechanical applications for numerous industrial and medical applications.

The primary problem with prior art, fiber optic imaging is that it is difficult to achieve acceptable measurement of surface tolerances or roughness through a single port or single optical fiber. Conventional fiber optic imaging also does not provide any quantitative measurement of the interior region being imaged. This is because prior art systems generally must rely on interferometry concepts requiring multiple fibers.

It is therefore an object of the present invention to provide profilometer apparatus for inspecting the interior surfaces of tanks and other device under tests, including medical implants and any enclosure having a single access port.

It is another object of the present invention to provide apparatus for inspecting interiors of tanks and other device under tests that is capable of accurate quantitative measurement of interior surface imperfections with a high degree of resolution.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, apparatus for inspecting the interior of a device under test through a single port in the device under test comprises laser means for producing laser energy, with beam splitter means for directing the laser energy to a first direction and to a second direction. Delay means receive the laser energy from the second direction for introducing an amount of controllable delay to the laser energy from the second direction and outputting the delayed laser energy from the second direction. Optical routing means receive the laser energy from the first direction for directing the laser energy from the first direction to ones of a first at least one optical fibers that enter the device under test through the port, and for transmitting laser energy reflected from interior surfaces of said device under test through the port, and for transmitting laser energy reflected from interior surfaces of the device under test to ones of a second at least one optical fibers. Elongate dye-cell means receive the laser energy reflected from the interior surfaces of the device under test at a first end and the delayed laser energy from the second direction at a second end for creating two-photon fluorescence between the laser energy reflected from the interior surfaces of the device under test and the delayed laser energy from the second direction and outputting the two-photon fluorescence, wherein the amount of controllable delay is representative of the interior surfaces of the device under test.

In a further aspect of the present invention, and in accordance with its objects and principles, a method for inspecting the interior surfaces of a device under test having a single entry port comprises the steps of launching laser energy into said device under test and into a delay circuit for introducing a controllable delay; receiving light reflected from the interior surfaces of the device into one end of an elongate dye cell; receiving the controllably delayed light into an opposite end of the elongate dye cell; adjusting the controllable delay so that two-photon fluorescence is emitted from a predetermined area of the elongate dye cell; analyzing the controllable delay to discern information about the interior surfaces of the device under test; and outputting the information about the interior surfaces of the device under test.

DETAILED DESCRIPTION

The present invention provides apparatus for the high resolution inspection of the interior of device under tests, having the capability of such inspection even should the device under test only have a single port of access. The invention can be understood most easily through reference to the drawings.

Figure 1:
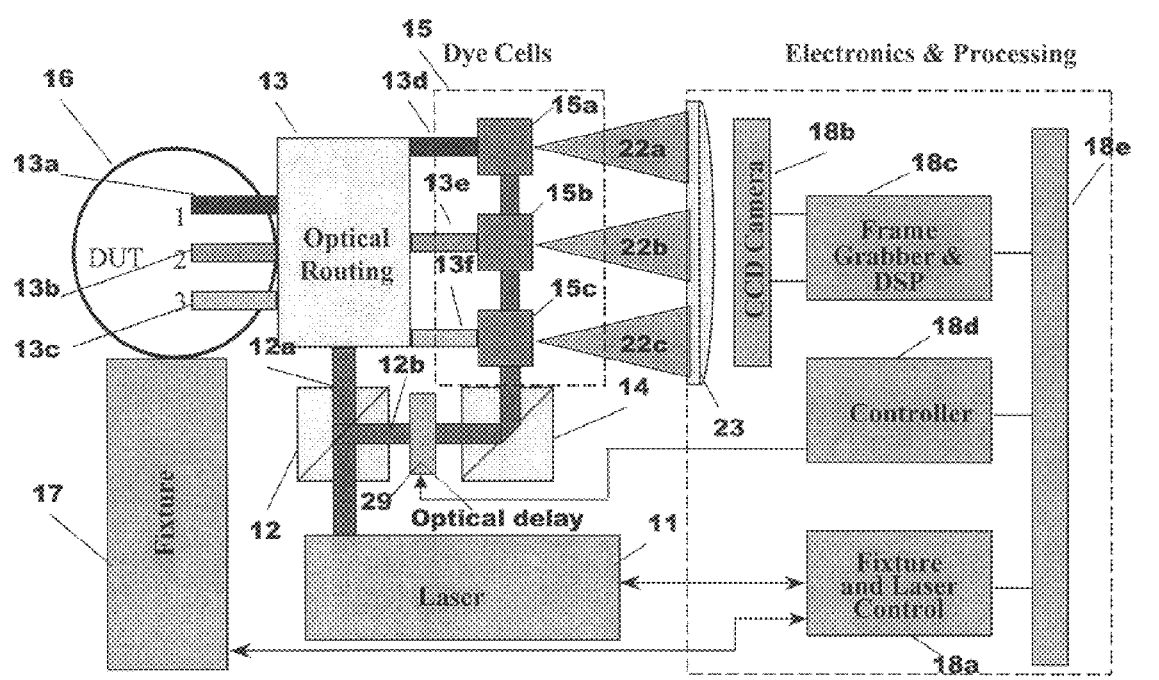
FIG. 1 is a block diagram illustrating the components of the present invention.

In FIG. 1, a block diagram of the components of the present invention is illustrated. As seen, laser system 11, which may be a Titanium doped Sapphire laser pumped by an Argon ion laser or a titanium-doped sapphire crystal excited by a frequency doubled, Nd doped, lithium vanadate laser, or any other appropriate laser outputting less than 100 femtosecond ($10^{-13}$ seconds) pulses to beamsplitter 12, which divides the pulse output of laser system 11 between optical path 12a and optical path 12b. However, as will be discussed below, many forms of laser energy with different modulation techniques can be used with the present invention. Optical path 12a carries a portion of the laser energy of laser system 11 to optical routing module 13. Optical fiber 12b carries the remaining portion of the laser energy output of laser system 11 to adjustable control line 28 by which the correlated output of laser system 11 in optical fiber 12b is controllably delayed before it is directed into correlation module 11 by mirror 14.

As will hereinafter be more particularly described, optical routing module 13 splits the pulses from beamsplitter 12 and directs them into inspection fibers 13a 13b, and 13c which are inserted into device under test 16. Device under test 16 is mounted onto fixture 17, which is capable of translating and rotating device under test 16, and which is itself controlled by fixture and laser control unit 18a. Fixture and laser control unit 18a indexes the rotational movement of fixture 17 and inserts inspection fibers 13a, 13b, and 13c into device under test 16 by an amount commensurate with the desired cross-sectional resolution of the profile measurement. Fixture and laser control unit 18a also controls the output of laser system 11, controlling such functions as pulse width and rate, or frequency (wavelength). The Fixture and laser control unit 18a, is in turn under the control of main controller 18d.

Optical routing module 13 serves several optical functions. Initially, optical routing module 13 directs the incident pulses output from laser system 11 into optical fibers 13a, 13b, and 13c for transmission to device under test 16. Optical routing module 13 also directs pulses returning from device under test 16 on optical fibers 13a, 13b, and 13c into optical fibers 13d, 13e, and 13f respectively. Optical fibers 13d, 13e, and 13f are routed to correlation module 15 and to individual dye cells 15a, 15b, and 15c, respectively.

Dye cells 15a, 15b, and 15c are elongate and can have a length of ten (10) to thirty (30) cm and have a cross-section of approximately thirty (30) cm. Each has transparent end windows made of any transparent material suitable for this application, with a fill hole in its top. Dye cells 15a, 15b, and 15c are filled with an appropriate dye solution. One such dye solution is a dilute ($10^{-4}$ to $10-5$ M) alcohol solution of an organic dye having the unique property of fluorescing at a wavelength one-half that of the pulses from laser system 11.

Figure 2:
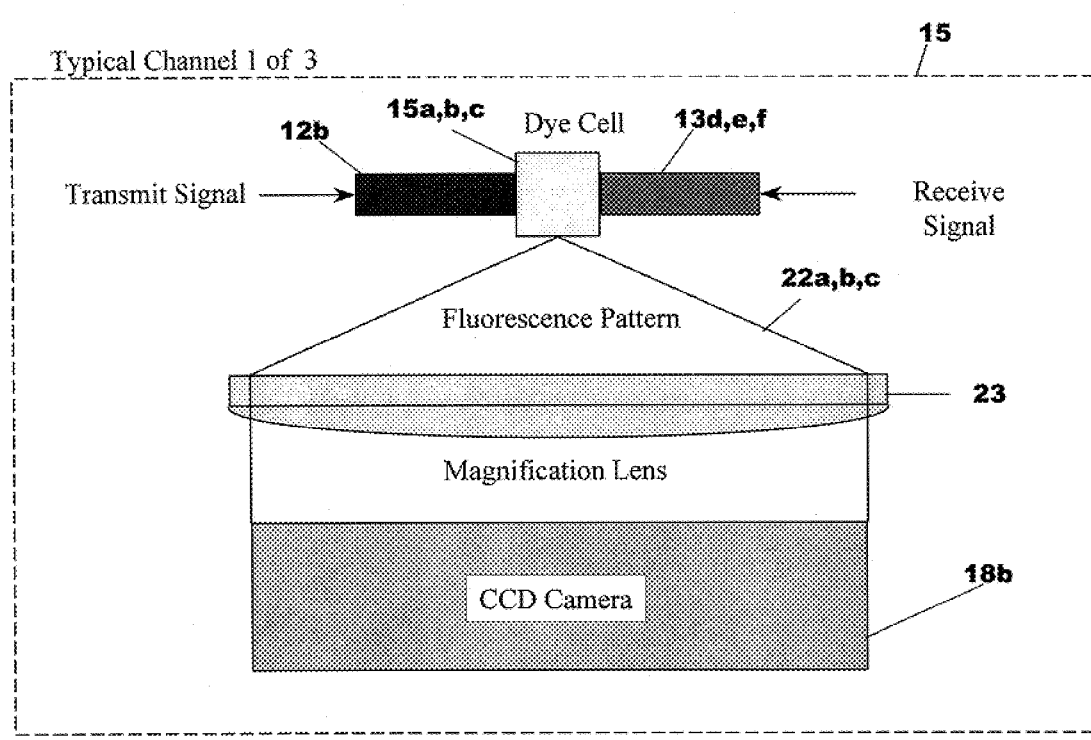
FIG. 2 is a schematical illustration of one of the dye cell units for output from the present invention.

As shown in FIG. 2, for an individual dye cell 15a, 15b, or 15c of correlation module 15, receive the signal reflected from the interior of device under test 16 (FIG. 1) which are on optical fibers 13d, 13e and 13f. Also input to dye cells 15a, 15b, or 15c is the controllably delayed transmitted signal on optical fiber 12b. The transmitted signal from laser system 11 (FIG. 1) on optical fiber 12b, is controllably delayed by adjustable delay line 28 (FIG. 1) so that its path can be equalized with the pulses returning from device under test 16 (FIG. 1). With the pulses on optical fiber 12b inserted into one end of dye cells 15a, 15b, and 15c, and the pulses on optical fibers 13d, 13e, and 13f inserted into the other end, the pulses will propagate toward each other in dye cells 15a, 15b, and 15c.

In the area of dye cells 15a, 15b, and 15c where the two pulses overlap, there is two-photon fluorescence emitted over the length of less than 30 $\mu$m (30 ×10–6 meters). There is no fluorescent output in any other area of dye cells 15a, 15b, and 15c. In practicing the invention, the two pulses are caused to overlap at one predetermined point by adjustment of adjustable delay line 28 by controller 18d (FIG. 1). The amount of delay imposed on pulses in optical fiber 12b to attain this overlap point is directly related to the interior surface features of device under test 16. The two-photon fluorescence emitted from dye cells 15a, 15b, and 15c is magnified by magnification lens 23. The magnified two-photon fluorescence is input to CCD camera 18b for conversion into an electrical signal representative of high-resolution inspection of the interior surface of device under test 16.

In operation, dye cells 15a, 15b and 15c serve to convert the optical energy in the pulses arriving from the transmit reference fiber, 12b and from the receive signals on optical fibers 13a, 13b, or 13c into two-photon fluorescence detectable by CCD camera 18b. The process of two-photon fluorescence accomplishes this task. Dye cells 15a, 15b and 15c in conjunction with adjustable time delay 28 (FIG. 1), provide a direct measure of the difference in total path difference between the transmit path through optical fibers 12a, and 13a, 13b, and 13c respectively, and the transmit reference path optical fiber 12b.

Figure 3:
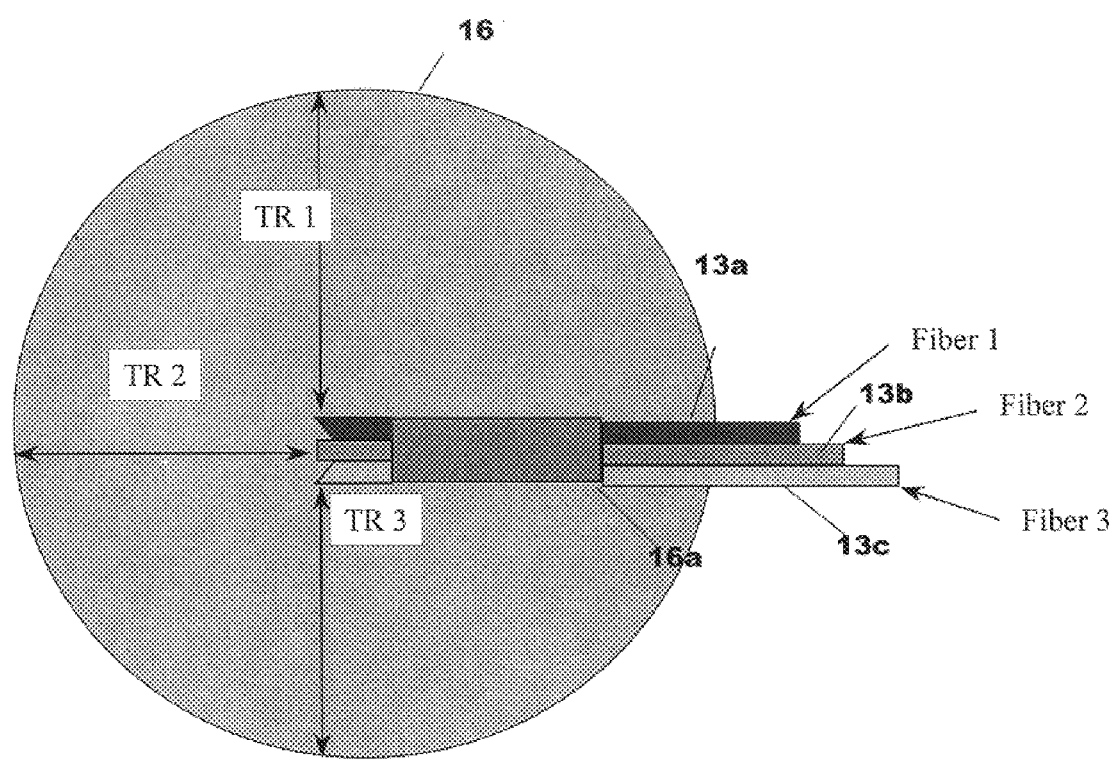
FIG. 3 is a side view detail of the end of three optical fibers inserted into a device under test to be inspected so that upon rotation and translation of the device under test virtually all of the interior surface can be inspected.

Turning now to FIG. 3, there can be seen optical fibers 13a, 13b, and 13c entering device under test 16 through a single port 16a. As shown, for illustrative purposes of one embodiment of the present invention, optical fibers 13a, and 13c have their ends finished to form a 45° reflector, with a high reflective coating applied to surfaces 31 and 32, and an anti-reflecting coating applied to surfaces 33 and 34. These coatings will direct light traveling along optical fibers 13a and 13c at a right angle to the longitudinal axes of optical fibers 13a and 13c. The end of optical fiber 13b, is finished at a 90° angle, and has an anti-reflective coating applied to its surface 35, to direct light along its longitudinal axis. With optical fibers 13a, 13b, and 13c so configured, virtually complete coverage of the interior surfaces of device under test E16 is possible when device under test 16 is rotated and laterally moved by fixture 17 (FIG. 1).

The use of the three fibers, optical fibers 13a, 13b, and 13c, with one cut at a 90° angle, and the second two cut at a 45° angle, is but one method to provide coverage of the internal volume of device under test 16. Another method of accomplishing this coverage involves cutting optical fibers 13a and 13c at angles other than 45°. This allows coverage of other areas of the interior surfaces of device under test 16 that might not be covered by optical fibers 13a, and 13c being cut at an angle of 45°.

Figures 4A, 4B:
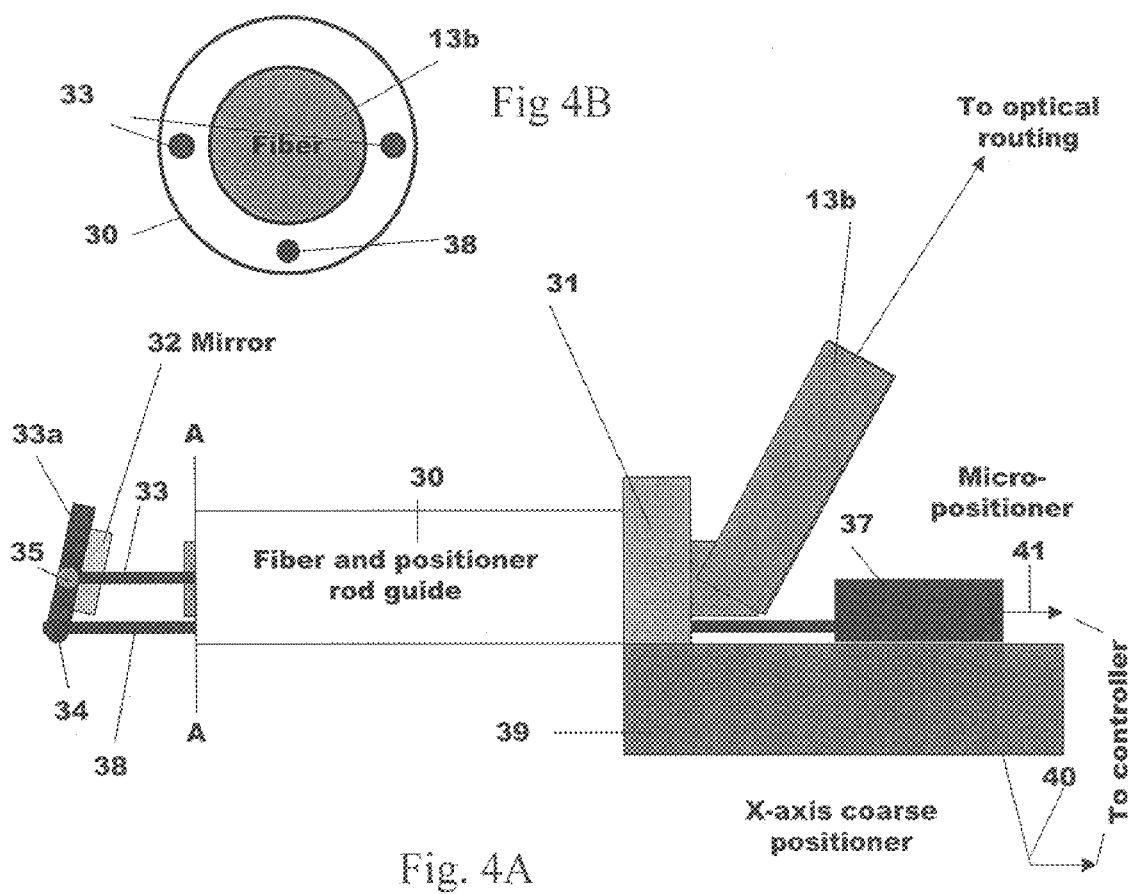
FIGS. 4A and 4B are schematical drawings of a micro-positioned mirror used to inspect the interior surface of a device under test instead of the ends of optical fibers.

Another embodiment of the present invention is shown in FIGS. 4A and 4B in which the provision of coverage of the interior surfaces of device under test 16 (FIG. 3) involves use of at least one micro-machine controlled mirror 32 to scan the internal surface of device under test 16 each through a single fiber such as optical fiber 13b illustrated. This micro-machine controlled mirror 32 could replace the optical fibers in device under test 16 in FIG. 1. FIG. 4B shows section A—A of FIG. 4A, an end view of fiber and positioner rod guide 30. This view clearly shows the relationship of fiber and positioner rod guide 30 with optical fiber 18b (in this case), scanner connectors 33, and micro-positioner rod 38.

In FIG. 4A, the side view illustrates how mirror 32 is attached to scanner plate 33a, which is held in moveable position by scanner rods 33 and micro-positioner rod 38. Scanner plate 33a is pivoted about rotation joints 34, 35. As seen, micro-positioner rod 38 is connected through fiber 31 and positioner rod guide 30 and bracket to micro-positioner 37. X-axis coarse positioner 40 is used to provide additional internal penetration of the interior surface of device under test 16. Both micro-positioner 41 and X-axis coarse positioner 40 are controlled by controller 18d (FIG. 1), which sends electrical signals that controls the amount of forward movement and the angle of mirror 32.

The interrogating laser pulse is transmitted through optical routing 13 (FIG. 1) to optical fiber 13b (for example) to mirror 32. Mirror 32 reflects the laser light to the interior surfaces of device under test 16 at different angles as determined by micro-positioner 41. Of course, in this embodiment, scanner plate 33a moves mirror 32 and its reflected laser light in a single plane. However, if device under test 16 can be rotated, then scanning of mirror 32 will achieve nearly complete coverage of the interior surfaces of device under test 16. In cases where device under test 16 cannot be rotated, mirror 32 could be axially rotated about fiber and positioner rod guide 30. This type of scanning would provide the same coverage as rotation of device under test 16.

Returning now to FIG. 1, it should be noted that the output of laser system 11 is modulated in order to facilitate analyzation of the signals returning from the interior surface of device under test 16. This modulation, which is applied prior to output from laser system 11, can be chosen from the group consisting of short pulse, frequency modulated continuous wave (FMCW) or chirp, and stepped frequency phase measurement. Each type of modulation has its own advantages, with the particular type dependent on the particular application. However, any one of these modulation techniques should provide satisfactory results with the present invention.

As stated, each of these modulation techniques has its own advantages. Short pulse modulation offers excellent resolution and direct measurement, but is somewhat complex and the pulse resolution is inversely proportional to pulse width. FMCW or chirp modulation, a linear chirp over the same bandwidth as short pulse modulation, has its resolution limited only by the total bandwidth, and accomplishes range measurement in the frequency domain, but is disadvantaged by the possibility its wide bandwidth can produce RF signals, and by its complexity in developing a high linearity sweep. Finally, stepped frequency phase measurement provides discrete wavelength, and accurate phase measurement. Its advantages are that the resolution is limited only by the total wavelength, and that range measurement is in the phase domain. Its disadvantages include that its resolution is limited by phase stability, and its high complexity in accurately measuring phase at optical wavelengths.

It is to be understood that the particular type of modulation employed in practicing this invention will require analysis of the requirements so that the correct modulation for the application can be utilized. It is a question of the resolution required or the amount of complexity allowed in the application. In the invention, the modulation of laser system 11 is provided through fixture and laser control 18a.

As illustrated for one dye cell in FIG. 2, fluorescence pattern 22 is imaged onto CCD camera 18b for each optical fiber 13a, 13b, and 13c shown in FIG. 1. CCD camera 18b provides its output to frame grabber and DSP (Digital Signal Processor) 18c for output.

Main controller 18d provides control to fixture and laser control 18a, to adjustable time delay 28, and to frame grabber and DSP 18c. The controller can be any general-purpose personal computer. Control bus 18c provides the connection between frame grabber and DSP 18c, main controller 18d and fixture and laser control 18 to provide the necessary communication between these devices.

Figure 5:
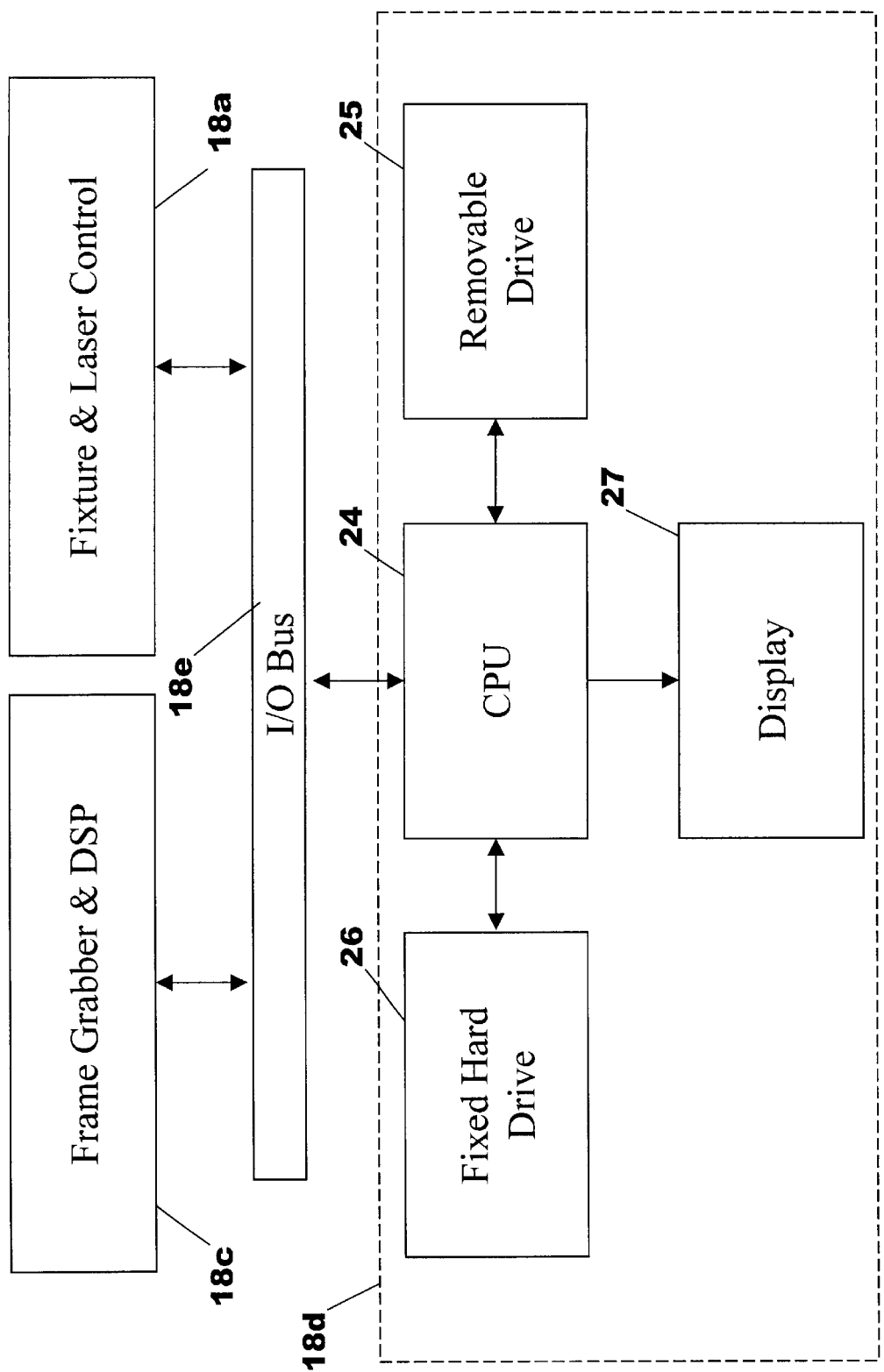
FIG. 5 is a block diagram of the control portion of the present invention and its interconnection to other control devices.

FIG. 5 is a block diagram of one embodiment of the computer control system for the present invention. As shown, fixture and laser control 18a and frame grabber and DSP 18c are connected to I/O bus 18e. Central processing unit 24 also is connected to I/O bus 18e as well as to removable hard drive 25, fixed hard drive 26, and display 27. Central processing unit 24 is programmed with the software necessary to provide the appropriate control signals to fixture and laser control 18a, frame grabber and DSP 18c, and adjustable delay line 28, and to analyze and display the signals returned to it from the interior surfaces of device under test 16 (FIG. 1).

The present invention can find application in numerous important areas. The inspection of interior surfaces of important vessel assemblies can further reduce the danger of vessel rupture and the concomitant dangers and expense. Devices intended for implantation into human bodies likewise must be examined so that any possible leakage is discovered and corrected prior to implantation. Thus, the present invention may prove to be invaluable in the discovery of surface problems in any vessel that has limited entry ports.

The foregoing description of the embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. Apparatus for inspecting the interior of a device under test through a single port in the device under test comprising:

laser means for producing laser energy;

beam splitter means for directing said laser energy to a first direction and to a second direction;

delay means receiving said laser energy from said second direction for introducing a an amount of controllable delay to said laser energy from said second direction and outputting said delayed laser energy from said second direction;

optical routing means receiving said laser energy from said first direction for directing said laser energy from said first direction to ones of a first at least one optical fibers that enter said device under test through said port, and for transmitting laser energy reflected from interior surfaces of said device under test to ones of a second at least one optical fibers;

elongate dye-cell means receiving said laser energy reflected from said interior surfaces of said device under test at a first end and said delayed laser energy from said second direction at a second end for creating two-photon fluorescence between said laser energy reflected from said interior surfaces of said device under test and said delayed laser energy from said second direction and outputting said two-photon fluorescence;

wherein said amount of controllable delay is representative of said interior surfaces of said device under test.

2. The apparatus as described in claim 1, further comprising fixture means for holding said device under test and for controllably positioning said device under test relative to said first at least one optical fibers.

3. The apparatus as described in claim 1, wherein said first and second at least one optical fibers each comprises three optical fibers.

4. The apparatus as described in claim 3, wherein said first at least one optical fibers comprise three optical fibers wherein two of said three optical fibers have ends that are cut at 45° angle surfaces and direct light at a right angle with respect to said light traversing said two of said three optical fibers.

5. The apparatus as described in claim 4, wherein said two optical fibers have reflective coating applied to said 45° angle surfaces.

6. The apparatus as described in claim 3, wherein said first at least one optical fibers comprise three optical fiber wherein two of said three optical fibers have ends that are cut at an angle of less than 45°.

7. The apparatus as described in claim 1, further comprising camera means in optical contact with said two-photon fluorescence for imaging said two-photon fluorescence and outputting said image.

8. The apparatus as described in claim 2, further comprising computer means receiving said image for displaying and analyzing said image, and for controlling said fixture means.

9. The apparatus as described in claim 1 wherein said laser energy is modulated using short pulse modulation.

10. The apparatus as described in claim 1 wherein said laser energy is modulated using frequency modulated continuous wave modulation.

11. The apparatus as described in claim 1 wherein said laser energy is modulated using stepped frequency phase measurement modulation.

12. The apparatus as described in claim 1 wherein said elongate dye-cell means is filled with a dilute alcohol solution of an organic dye that fluoresces at a wavelength of one-half that of said laser energy.

13. The apparatus as described in claim 1 wherein said laser means comprise a titanium-doped sapphire crystal excited by a frequency doubled, Nd doped, lithium vanadate laser.

14. The apparatus as described in claim 1 wherein said first at least one optical fiber connect to a scanning at least one micro-positioned mirror for reflecting laser energy to interior surfaces of said device under test and reflecting laser energy reflected from said interior surfaces into said first at least one optical fiber.

15. The apparatus as described in claim 14, wherein said at least one micro-positioned mirror is rotatable about its axis.

16. A method of inspecting the interior surfaces of a device under test having a single entry port comprising the steps of:

launching laser energy into said device under test and into a delay circuit for introducing a controllable delay;

receiving light reflected from said interior surfaces of said device into one end of an elongate dye cell;

receiving said controllably delayed light into an opposite end of said elongate dye cell;

adjusting said controllable delay so that two-photon fluorescence is emitted from a predetermined area of said elongate dye cell;

analyzing said controllable delay to discern information about said interior surfaces of said device under test; and outputting said information about said interior surfaces of said device under test.

17. The method as described in claim 16, further comprising the step of rotating and translating said device under test.

18. The method as described in claim 17, further comprising the step of directing said light toward virtually all of said interior surfaces.

19. The method as described in claim 16 wherein said laser energy is modulated using short pulse modulation.

20. The method as described in claim 16 wherein said laser energy is modulated using frequency modulated continuous wave modulation.

21. The method as described in claim 16 wherein said laser energy is modulated using stepped frequency phase measurement modulation.

* * * * *